US006589929B2

(12) United States Patent
De Lima et al.

(10) Patent No.: US 6,589,929 B2
(45) Date of Patent: *Jul. 8, 2003

(54) ENZYME-CONTAINING GRANULES AND PROCESS FOR THE PRODUCTION THEREOF

(75) Inventors: Joao F. De Lima, Birkerod (DK); Eder Manzini Bordin, Curitiba (BR); Erik Kjaer Markussen, Vaerlose (DK); Kirsten Boegh Levring, Virum (DK); Michael Bonde, Lyngby (DK); Erik Marcussen, Ballerup (DK); Grethe Saugmann, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/101,123

(22) Filed: Mar. 19, 2002

(65) Prior Publication Data

US 2002/0173441 A1 Nov. 21, 2002

Related U.S. Application Data

(63) Continuation of application No. 09/548,832, filed on Apr. 13, 2000, now Pat. No. 6,403,549, which is a division of application No. 08/856,165, filed on May 14, 1997, now Pat. No. 6,136,772, which is a continuation of application No. PCT/DK97/00161, filed on Apr. 4, 1997.
(60) Provisional application No. 60/029,738, filed on Oct. 23, 1996.

(30) Foreign Application Priority Data

Apr. 12, 1996 (DK) .......................... 1996 00420
Jul. 5, 1996 (DK) .......................... 1996 00759

(51) Int. Cl.[7] ............................ C11D 3/386; C11D 3/22; C11D 3/382
(52) U.S. Cl. ........................ 510/392; 510/438; 510/442; 510/446; 510/530; 435/187
(58) Field of Search ................... 510/392, 438, 510/442, 446, 530; 435/187

(56) References Cited

U.S. PATENT DOCUMENTS

| | | | |
|---|---|---|---|
| 3,223,593 A | 12/1965 | Aldrich et al. ................ 195/63 |
| 3,723,327 A | 3/1973 | van Kampen et al. ...... 252/110 |
| 4,418,147 A | * 11/1983 | Muetgeert et al. .......... 435/178 |
| 4,526,698 A | 7/1985 | Kuroda et al. ................ 252/99 |
| 4,551,389 A | 11/1985 | Ohtake et al. ............... 428/402 |
| 4,663,447 A | 5/1987 | Yamazaki et al. ............. 536/76 |
| 5,049,394 A | 9/1991 | Howard et al. .............. 424/490 |
| 5,204,108 A | 4/1993 | Illum ........................ 424/434 |
| 5,254,283 A | * 10/1993 | Arnold et al. ......... 252/174.12 |
| 5,268,286 A | 12/1993 | Kobayashi et al. .......... 435/178 |
| 5,324,649 A | 6/1994 | Arnold et al. ............... 435/187 |
| 5,364,634 A | 11/1994 | Lew ........................... 424/451 |
| 5,543,155 A | 8/1996 | Fekete et al. ................ 424/473 |
| 6,136,772 A | * 10/2000 | De Lima et al. ............. 510/392 |
| 6,403,549 B1 | * 6/2002 | De Lima et al. ............. 510/392 |

FOREIGN PATENT DOCUMENTS

| | | |
|---|---|---|
| CA | 1313154 | 1/1993 |
| EP | 0 363 874 | 4/1990 |
| EP | 0 454 044 | 10/1991 |
| EP | 0 532 777 | 3/1993 |
| WO | WO 94/26883 | 11/1994 |
| WO | WO 95/22318 | 8/1995 |

OTHER PUBLICATIONS

Dialog accession No. 007054253, Abstract of JP 62–011093 Jan. 20, 1987.
Dialog accession No. 010766827, Abstract of JP 81–09126 Apr. 30, 1996.
Dialog accession No. 010108289, Abstract of JP 62–93635 No date Given.
Dialog accession No. 01559484, Abstract of JP 60–037984 Feb. 27, 1985.

* cited by examiner

Primary Examiner—Yogendra N. Gupta
Assistant Examiner—Brian P. Mruk
(74) Attorney, Agent, or Firm—Elias Lambiris; Jason Garbell

(57) ABSTRACT

The present invention relates to enzyme-containing granules comprising (a) an enzyme and (b) a core which intrinsically is capable of absorbing at least 5% w/w (based on the weight of the core) of water and to processes for the production of such granules comprises (a) contacting absorbent cores, capable of absorbing at least 5% w/w (based on the weight of the core) of water, with a liquid medium, such as an aqueous medium, containing an enzyme in dissolved and/or dispersed form, the amount of the liquid medium employed being such that substantially no attendant agglomeration of the resulting product occurs; and (b) at least partially removing volatile components of the liquid medium from the resulting product.

20 Claims, No Drawings

ENZYME-CONTAINING GRANULES AND PROCESS FOR THE PRODUCTION THEREOF

CROSS-REFERENCE TO RELATED APPLICATIONS

This application is a continuation of U.S. application Ser. No. 09/548,832 filed on Apr. 13, 2000 now U.S. Pat. No. 6,403,549 which is a division of Ser. No. 08/856,165 filed on May 14, 1997, now U.S. Pat. No. 6,136,772 which is a continuation of PCT/DK97/00161 filed Apr. 4, 1997 and claims priority under 35 U.S.C. 119 of Danish applications 0420/96 and 0759/96 filed Apr. 12, 1996 and Jul. 5, 1996, respectively, and of U.S. application 60/029,738 filed Oct. 23, 1996, the contents of which are fully incorporated herein by reference.

FIELD OF THE INVENTION

The present invention relates to an enzyme-containing granulate (made up of enzyme-containing granules or particles) with extremely low tendency to dust formation, to a process for producing such a granulate, and to the use of said granulate for a number of industrial applications.

BACKGROUND OF THE INVENTION

The industrial use of enzymes, notably enzymes of microbial origin, has become increasingly common. Enzymes are used in numerous industries, including, for example, the starch-processing industry and the detergent industry. It is well known that the use of enzymes, particularly proteolytic enzymes, in the detergent industry has given rise to industrial hygiene concerns for detergent factory workers, particularly due to the health risks (including the risk of allergy development) associated with any formation of enzyme-containing dust which may occur.

Since the introduction of enzymes into the detergent industry, a lot of effort has been devoted to improving the granulation and coating of enzymes so as to reduce enzyme dust formation.

One type of process for producing an enzyme-containing granule comprises coating the surface of a core with an enzyme followed by an outer layer coating. U.S. Pat. No. 5,324,649 describes coating of the surface of a non-pareil core with an enzyme followed by an outer layer coating. U.S. Pat. No. 4,689,297 and EP 0 532 777 describe a process which comprises applying an enzyme on the surface of a salt crystal based core or a non-pareil core, by spraying the enzyme onto the core in a fluid-bed followed by an outer layer coating.

Yet another type of process essentially comprises: (i) mixing an enzyme with suitable granulation components (preferably as dry matter), such as filler, binder, fibrous material and a granulation agent (e.g. water) in a granulator (e.g. a mixer), and (ii) processing the mixture in a granulating apparatus until the granule has the desired particle distribution and degree of roundness (sphericity).

Numerous references describe processes for making enzyme-containing granules by such a process. Such references include U.S. Pat. No. 4,242,219, U.S. Pat. No. 4,740,469, WO 94/04665, U.S. Pat. No. 4,940,665, EP 564476, EP 168526, U.S. Pat. No. 4,661,452, U.S. Pat. No. 4,876,198, WO 94/16064 and U.S. Pat. No. 4,106,991.

Further, U.S. Pat. No. 5,494,600 and U.S. Pat. No. 5,318,903 describe a process comprising absorption of an enzyme into a porous hydrophobic core (e.g. a porous hydrophobic silica core) followed by coating.

Although granulation techniques have improved, in order to take account of increasing environmental concerns and heightened awareness in the field of industrial hygiene, there remains a continuing need for enzyme-containing, granular compositions exhibiting even lower dust formation than presently available products.

An object of the present invention is to provide such enzyme-containing granular compositions, and improved processes for producing such compositions.

SUMMARY OF THE INVENTION

It has surprisingly been found that extremely low tendency to dust formation by enzyme-containing granules is achievable when the granules are based on suitably selected cores (particles), more specifically cores fulfilling, in particular, certain requirements with respect to liquid-absorption properties.

A first aspect of the present invention thus relates to an enzyme-containing granule comprising:
 (a) an enzyme, and
 (b) a core which intrinsically is capable of absorbing at least 5% by weight (w/w) of water (relative to the weight of the core).

In keeping with this first aspect of the invention, a further aspect of the invention relates to a process for producing enzyme-containing granules from absorbent cores, the process comprising:
 (a) contacting absorbent cores, capable of absorbing at least 5% w/w (based on the weight of the core) of water, with a liquid medium containing an enzyme in dissolved and/or dispersed form, the amount of the liquid medium employed being such that substantially no attendant agglomeration of the resulting product occurs; and
 (b) at least partially removing volatile components of the liquid medium from the resulting product.

DETAILED DESCRIPTION OF THE INVENTION

Cores

Cores forming the basis of enzyme-containing granules of the invention (and in the context of processes according to the invention for the preparation of such granules) are cores which, in the absence of a hydrophobicity-reducing substance or surface-tension-reducing substance (such as a surfactant) and of constituents of the enzyme-containing granules (notably the enzyme or enzymes in question) other than those of the core itself, have an intrinsic (i.e. inherent, innate or "native") ability to absorb at least 5% w/w of water when brought into contact with water (i.e. essentially pure, liquid water).

Cores of relevance in the context of the invention are preferably capable of absorbing at least 10% w/w (based on core weight) of water, more preferably at least 15% w/w and still more preferably at least 20% w/w. Particularly preferable cores are cores capable of absorbing at least 30% w/w of water, such as cores capable of absorbing at least 33% w/w. Certain preferred types of cores have an even greater water-absorption capacity (e.g. about 40% w/w or more of water).

The ability of a particular type of core to absorb water may suitably be determined, for example, by spraying a measured amount of water onto a measured amount of cores with mixing in a mixer [e.g. as described in Example 1 herein (vide infra)] and observing the appearance and behaviour of the cores in the course of spraying; ambient conditions (ambient temperature, pressure etc.) are generally suitable. In general, as long as the amount of cores in question is able to absorb water there is essentially no agglomeration of the wetted cores (i.e. agglomeration to form lumps or the like) and it is possible to remove the resulting individual particles and dry them without significantly changing the overall particle size distribution.

In the context of the invention, a quoted weight percentage of water which a given type of core is capable of absorbing is thus a "macroscopic", overall value determined using a relatively large amount (and thereby a large number) of cores (particles) of the given type, such as a multi-kilogram quantity (e.g. an amount of about 5, 10, 15 or more kilograms of the given type of core).

If appropriate, smaller quantities of cores may, however, be employed for the determination of water-absorption capacity, provided (i) the number of individual core particles in the sample employed is sufficiently high to be adequately representative of the bulk cores, and (ii) the sample employed is sufficiently large to permit satisfactorily gradual addition of water (preferably by spraying), with adequate mixing, while observing the appearance/behaviour of the cores with respect to surface wetness and tendency to agglomerate.

With a poorly absorbing or non-absorbing core material, agglomeration of the granules will normally occur upon introduction of only a small amount of water, and consequently it will generally not be possible to maintain the initial overall particle size distribution.

An example of a poorly absorbing core material is a conventional sugar/starch-based particle of the so-called nonpareil type. In working examples herein (vide infra) it is shown, inter alia, that a typical nonpareil core product is able to absorb less than 4% of water by weight (relative to the core).

Preferred embodiments of enzyme-containing granules of the invention are granules wherein at least part of the total amount of enzyme present in the granule is absorbed within the core; such granules will often be granules wherein at least part of the total amount of enzyme present in the granule has been absorbed into the core via contact of the outer surface of the core with a liquid medium containing the enzyme in question.

Such embodiments appear [cf. the working examples herein (vide infra)] to be advantageous in relation to achieving improvement in a number of characteristics or properties of enzyme-containing granules of the invention relative to enzyme-containing granules of known types; these characteristics or properties include:

tendency of the granules to form dust (particularly enzyme-containing dust);

enzymatic activity yield of the granules (i.e. degree of retention, in a batch of product granules, of the total original enzymatic activity of the enzyme preparation used to prepare the batch);

degree of retention of enzymatic activity during storage of the granules under various conditions; and degree of retention of enzymatic activity following aggressive treatments such as exposure to high temperatures and/or high humidity.

Moreover, without being bound to any theory it is believed [as also mentioned below (see Example 11 herein)] that the presence, within the core, of absorbed enzyme enhances the adherence of enzyme deposited on the outer surface of an absorbent core of the type of relevance in the context of the invention, leading to corresponding reduction in the tendency to dust formation by such a product.

In relation to embodiments of enzyme-containing granules of the invention wherein a part of the total enzyme content is absorbed within the core, valuable embodiments include those wherein at least 10% w/w, such as at least 25% w/w, e.g. at least 40% w/w of the total enzyme content (calculated as active enzyme protein) is present as enzyme absorbed within the core.

Particularly valuable embodiments include those wherein at least 90% w/w of the total enzyme content of the granule is present as enzyme absorbed within the core, and it is possible (employing, e.g., a process according to the invention) to obtain enzyme-containing granules of the invention in which essentially all (i.e. essentially 100% w/w) of the enzyme content of the granule is present as enzyme absorbed within the core.

In may be mentioned this connection that for a given distribution of the enzyme content of granules of the invention between (i) core-absorbed enzyme and (ii) enzyme present on the surface of the core or in/on one or more coating layers, the absolute amount of enzyme protein which is present as enzyme absorbed within the core will, of course, depend on the total amount of enzyme present in the granule.

Cores forming the basis of enzyme-containing granules of the invention, and cores employed in the process according to the invention, are preferably shaped so that the ratio between the largest and the smallest diameter thereof is less than 3; granules of the invention—whether uncoated or coated (vide infra)—are likewise preferably shaped so that the ratio between the largest and the smallest diameter thereof is less than 3. For both cores and enzyme-containing granules, the latter ratio is preferably less than 2, more preferably $\leq 1.5$ (i.e. between 1 and 1.5), and it is particularly preferred that the ratio in question is at most 1.2.

In should be noted that in the context of the present invention, values of the above-mentioned ratio between the largest and the smallest diameters of cores or granules as recited herein are normally determined as the mean value of the ratio in question for a representative number of particles taken at random from a sample of the cores or granules in question. For the majority of preferred types/shapes of cores or granules in the context of the invention, measurement of the ratio in question (e.g. by microscopy) for each of 20 or more particles taken at random from a sample of cores or granules, respectively, provides a reliable basis for calculating a satisfactorily reproducible mean value.

For most purposes, cores forming the basis of enzyme-containing granules of the invention, cores employed in the process according to the invention, as well as enzyme-containing granules of the invention perse, are substantially spherical, i.e. such that the ratio in question is about 1 (in that for a strictly spherical particle, the ratio in question is of course 1.0).

The ratio between the largest and the smallest diameter of a core or a granule may in general be taken as the ratio between the largest and the smallest dimension (linear dimension) of the core or the granule, respectively, in a direction passing substantially through the center of the particle.

With regard to the term "center of the particle" it will be apparent that particles (cores or granules) which are substantially axially symmetric, such as substantially spherical or ellipsoidal particles, will have a geometrically rather well-defined center. In such cases the term "center of the particle" may be interpreted in a geometric manner.

Particles of more irregular shape will, however, in general not have a geometrically definable center, and in such cases the "center of the particle" may [in that irregularly shaped particles (cores, granules) are—for most purposes—generally not preferred types in the context of the invention] be understood to be the center of gravity of the particle in question.

It is further preferred that cores forming the basis of enzyme-containing granules of the invention, cores employed in the process according to the invention, as well as enzyme-containing granules of the invention per se [whether the granules are uncoated or coated (vide infra)] have a substantially smooth surface, i.e. a surface which is essentially free of protuberances, spikes, secondary particles, irregularities, cavities, craters, indentations, pits and the like.

The degree of "smoothness" of cores or granules in the context of the invention will, in general, be based on an overall assessment of the surface characteristics of a representative sample of bulk cores or granules, respectively. Particularly in the context of particles (cores or granules) which are substantially spherical, the term "smooth" may further be taken to indicate that the mean value, for a representative number (e.g. $\geq 20$ particles), of the ratio between the largest and the smallest linear dimension of the particles, in a direction passing through the center of the particle, and measured on any given partial segment of the outer surface of the particle, is less than 1.15, preferably less than 1.10, and more preferably less than 1.05.

Preferred types of cores in the context of the invention include cores comprising starch and/or modified starch, notably cores containing a total of at least 25% w/w (based on total core weight), such as at least 50% w/w, of starch and/or modified starch.

Enzyme-containing granules based on cores comprising a total of at least 75% w/w of starch and/or modified starch, e.g. a total of at least 80% w/w, such as a total of at least 85% w/w (based on total core weight) of starch and/or modified starch, appear, in general, to possess particularly advantageous properties (e.g. properties such as low tendency to dust formation, heightened retention of enzyme activity, etc, as discussed earlier, above).

Highly preferred cores of this type are cores containing a total of at least 90% w/w, particularly at least 95% w/w (based on total core weight), of starch and/or modified starch, especially cores consisting essentially exclusively of (i.e. containing a total of essentially 100% w/w of) starch and/or modified starch.

It will be apparent that the above-mentioned total weight percentages (% w/w) of starch and/or modified starch are expressed as percentages of the weight of the core(s) per se, [i.e. the cores in their "native" or innate state, not including the enzyme and/or any other components which enter or adhere to the core(s) in the course of preparation of enzyme-containing granules in accordance with the invention].

Starches (naturally occurring starches) from a wide variety of plant sources appear to be suitable in the context of the invention (either as starches perse, or as the starting point for modified starches), and relevant starches include starch from: cassava [notably from bitter cassava (*Manihot esculenta*) or sweet cassava (*Manihot dulcis*)]; sago-palm (Metroxylon spp., such as *M. sagu*); potato (*Solanum tuberosum*); rice (Oryza spp.); corn (maize, *Zea mays*); wheat (Triticum spp.); barley (Hordeum spp., such as *H. vulgare*) sweet potato (*Ipomoea batatas*); sorghum (Sorghum spp.); and yam (Dioscorea spp.).

Other types of starch of potential value in the context of the invention include starch from: rye (*Secal cereale*); oat (Avena spp., such as *A. sativa*); millet (e.g. from species of Digitaria, Panicum, Paspalum, Pennisetum or Setaria); buckwheat (Fagopyrum spp., such as *F. esculentum*); waxy maize; other cereals; arrowroot (e.g. *Maranta arundinacea*); taro (Colocasia spp., such as *C. antiquorum* or *C. esculenta*); tannia (*Xanthosoma sagittifolium*); Amaranthus spp.; and Chenopodium spp.

Cassava starch is among preferred starches in the context of the invention; in this connection it may be mentioned that cassava and cassava starch are known under various synonyms, including tapioca, manioc, mandioca and manihot.

As is well known, starches consist, in general, essentially of macromolecular polymers composed of α-D-glucopyranose units. Linear or substantially linear polymeric forms in which these units are linked by α-D-(1→4) linkages are known as "amylose". Branched polymeric forms containing α-D-glucopyranose units linked by both α-D-(1→4) and α-D-(1→6) linkages are known as "amylopectin", the α-D-(1→6) linkages accounting typically for about 5–6% of the glycosidic linkages therein.

In this connection, starches from different vegetable sources contain different proportions of amylose and amylopection. Thus, for example, starch from potatoes typically contains ca. 20% w/w of amylose and ca. 80% w/w of amylopectin, whereas so-called "waxy maize starch" generally contains $\leq 2\%$ w/w of amylose and >98% w/w of amylopectin.

In relation hereto it may be mentioned that a considerable amount of effort has been expended with a view to obtaining strains (e.g. genetically manipulated strains) of starch-producing plants which can produce starches having an altered amylose/amylopectin balance (ratio) relative to that of starch produced by the plant as it occurs in nature.

Starches having widely differing proportions of amylose and amylopectin, respectively, are believed to be of value in the context of the present invention. Thus, high-amylose starches, high-amylopectin starches, and starches having intermediate amylose/amylopectin ratios—including starches from genetically modified plant sources—are all of relevance in the context of the invention, either as starches per se or as sources of modified starches.

As employed in the context of the present invention, the term "modified starch" denotes a starch (native starch) which has undergone some kind of at least partial chemical modification, enzymatic modification, and/or physical or physicochemical modification, and which—in general—exhibits altered properties relative to the "parent" starch.

Relevant chemical modifications include, but are not limited to: esterification of hydroxy groups (achieved, e.g., via acetyl-ation); etherification of hydroxy groups; oxidation (achieved, e.g., via reaction with chlorine or hypochlorite); and cross-linking (achieved, e.g., by reaction with formaldehyde or epichlorohydrin).

Etherified starches (e.g. carboxymethyl-starches or hydroxyalkyl-starches) and/or esterified starches can serve, inter alia, as binders (vide infra) in cores of relevance in the context of the invention.

Relevant enzymatic modifications include, for example, treatment with a starch-degrading or starch-modifying enzyme, e.g. an amylase, such as an α-amylase or glucoamylase. In this connection, a particularly interesting possibility is modification of the absorption properties (and possibly other properties) of existing starch-containing cores, including cores consisting predominantly or essentially exclusively of starch and/or partly gelatinized starch (vide infra), by controlled treatment thereof with a starch-degrading enzyme so as to modify (normally increase), the porosity/absorption capacity of cores [for example via the creation of new pores, and/or via an increase in the size and/or number and/or extent ("depth") of existing pores therein].

Relevant physical or physicochemical modifications include, in particular, so-called gelatinization. The term "gelatinized", in the context of starch, is used herein in accordance with usage in the art (see, e.g., A. Xu and P. A. Seib, *Cereal Chem.* 70 (1993), pp. 463–70).

When a core comprising a porous aggregate of starch grains is partly gelatinized (e.g. by heating under water vapour pressure), it is believed that the starch grains situated at or near the outer surface of the core undergo a process wherein the amylose and/or amylopectin in the grains in question forms an internal network/structure which results in greater elasticity and physical strength of the outer part of the core.

The degree of gelatinization may suitably be determined using differential scanning calorimetry (DSC) as described by A. Xu and P. A. Seib (loc cit.) (see Example 21 herein for further details).

In a further aspect of the invention, very useful cores of the type (discussed above) comprising starch and/or modified starch are cores which comprise partly gelatinized starch; preferred cores of this type include cores consisting essentially exclusively of partly gelatinized starch.

In such cores it is generally desirable that the degree of gelatinization (vide infra) of the starch is greater than 0.5%, such as at least 2%, and at most 95%. For many types of starch, a preferred range of degree of gelatinization in this connection is from 10% to 60% gelatinization.

Starch-containing cores with very low degrees of starch gelatinization appear to have lower physical strength than corresponding cores with high degrees of starch gelatinization. On the other hand, the water-absorption ability of starch-containing cores with high degrees of starch gelatinization appears to be lower than for cores with lower degrees of starch gelatinization.

Particularly—but not exclusively—in the case of cores consisting predominantly, or essentially solely, of partly gelatinized starch, degrees of starch gelatinization in the range of 30–60%, such as in the range of 30–50%, appear to be associated, inter alia, with a combination of very satisfactory absorption capacity, a high degree of sphericity and surface smoothness, and satisfactorily high physical strength (resistance to crushing). As is apparent from the working examples herein (vide infra), starch-based cores of this type can be supplied by existing suppliers, and have been found to exhibit a very desirable combination of properties in the context of numerous aspects within the scope of the present invention.

In connection with the use, in particular, of starches as core materials in the context of the invention, it is contemplated that as an alternative to substantially homogeneous, starch-based core particles it will be possible to employ core particles which comprise a layer of absorbent starch (e.g. cassava starch or rice starch) deposited on an inner carrier material (e.g. an insoluble silicate, carbonate or the like) which may or may not itself possess the water-absorption properties which are otherwise characteristic of cores in the context of the invention.

In this connection, further types of absorbent cores which appear to be suitable in the context of the invention include cores comprising a non-hydrophobic silicate or siliceous material as an absorbent material. Examples of such materials which may be prepared in, or are available in, granular form are bentonite, fuller's earth (both of which consist predominantly of the smectite mineral montmorillonite), diatomaceous earths (infusorial earths, e.g. kieselguhr, tripolite, tripoli or diatomite) and other smectite minerals (such as beidellite, nontronite, saponite, sauconite or hectorite).

Cores forming the basis of enzyme-containing granules according to the invention, or employed in the process of the invention, may—where appropriate and relevant—comprise one or more materials (additives or adjuvants) such as binders, fillers, plasticizers, fibrous materials and/or so-called "superabsorbents".

Binders: When incorporated in cores in the context of the invention, binder(s) will suitably be present in amounts constituting up to about 20% of the total weight of the core. Appropriate binders will generally be binders which are conventionally used in the field of granulation and which have a high melting point, or do not melt, and are of a non-waxy nature. Such binders may be low or high molecular weight binders, including water-soluble binders and water-based emulsion binders. Included in this connection are carbohydrate-type binders ranging from substances of the monosaccharide type to substances of the polysaccharide type, as well as derivatives thereof. Oligosaccharide-type binders, e.g. certain dextrins, are often well suited.

Examples of binders of the polysaccharide derivative type include starch derivatives (some types of which have already been mentioned above in connection with modified starches), such as starch esters (e.g. starch acetate), starch ethers (such as carboxymethyl-starch or hydroxyalkyl-starches, e.g. hydroxymethyl-, hydroxyethyl- or hydroxypropyl-starch) and cellulose derivatives, such as methylhydroxypropyl-cellulose, hydroxypropyl-cellulose, methyl-cellulose, carboxymethyl-cellulose (CMC) as well as CMC sodium salt.

Further examples of relevant binders include polyacrylates, polymethacrylates, acrylic acid/maleic acid copolymers and vinyl-group-containing compounds, such as polyvinyl alcohol, hydrolysed polyvinyl acetate and polyvinylpyrrolidone.

Fillers: Fillers appropriate for incorporation in cores in the context of the present invention include inert materials used to add bulk and reduce cost, or used for the purpose of adjusting the intended enzyme activity in the finished granulate. Examples of such fillers include, but are not limited to, water-soluble substances such as urea, various salts (such as sodium chloride, ammonium sulphate or sodium sulphate) and sugars, and water-dispersible agents such as clays, talc, silicates or starches.

Plasticizers: In certain types of cores of relevance in the context of the invention, plasticizer(s) may suitably be present in amounts constituting up to about 10% of the total weight of the core. Plasticizers serve generally to reduce brittleness and/or enhance deformability, and will typically be low molecular weight organic compounds of low volatility [such as polyols (e.g. glycols such as ethylene glycol), urea and phthalate esters (such as dibutyl or dimethyl phthalate)]. Water may in some cases serve as a plasticizer.

Fibrous materials: When incorporated in cores in the context of the invention, fibrous material(s) will suitably be present in amounts constituting up to about 30% of the total weight of the core, preferably between 5 and 15%. Suitable fibrous materials include materials which have high tensile strength and are in the form of fine filaments having a diameter of 1–50 $\mu$m and a length equal to at least four diameters. Typical fibrous materials include, but are not limited to: cellulose fibres, glass fibres, metal fibres, rubber fibres, azion fibres (manufactured from naturally occurring proteins from corn, peanuts and milk) and synthetic polymer fibres (such as fibres of Rayon™, Nylon™, polyester, polyolefin, Saran™, Spandex™ and vinal™. Cellulose fibres are very suitable fibres in this connection, and will often suitably have an average fibre length in the range of 150–300 μm and a diameter in the range of about 20–40 μm.

Superabsorbents: Certain types of—in particular—macro-molecular substances possess the ability to absorb many times their own weight of water or certain aqueous media. Substances of this type [which include various types of synthetic polymers as well as substances derived from polymers of natural origin, and which have found applications, for example, as body fluid absorbents (e.g. in wound dressings, diapers, sanitary towels and the like)] are sometimes referred to as "superabsorbents", and such substances may be present as a component of cores which form the basis for enzyme-containing granules of the invention.

One group of interesting superabsorbent materials, described in WO 96/03440, comprises readily biodegradable substances derived—via an enzymatic process—from certain naturally occurring phenolic polysaccharides, such as phenolic pectins, and such substances are well suited as water-absorbent components in cores of relevance in the context of the invention.

At this point it is appropriate to mention another class of absorbent cores which are well suited as the basis for enzyme-containing granules of the invention, namely "placebo" (enzyme-free) cores prepared in accordance with the general methodology of U.S. Pat. No. 4,106,991 but without the inclusion of an enzyme. U.S. Pat. No. 4,106,991 describes the production of so-called "T-granulates" comprising—in addition to enzyme—2–40% w/w of fibrous cellulose, together with binder (e.g. one of those mentioned above in the context of binders for cores or relevance in the context of the invention), filler (typically a salt such as sodium sulphate or sodium chloride, optionally together with a minor proportion of a whitener such as titanium dioxide or kaolin) and a liquid-phase granulating agent (water and/or a waxy substance such as a polyglycol, fatty alcohol, ethoxylated fatty alcohol or the like). By preparing granulates in accordance with U.S. Pat. No. 4,106,991 (which employs drum granulation of a mixture of enzyme, fibrous cellulose, binder, filler, and liquid-phase granulating agent), but without incorporation of enzyme, absorbent cores which are well suited as cores in the context of the present invention may be prepared. Cores of this type, which may appropriately be termed "placebo T" cores, may also be prepared using "filler" materials other than salts (such as powdered starch, e.g. powdered rice starch).

As already indicated to some extent above, it is preferable that core particles forming the basis of enzyme-containing granules of the invention have relatively high physical strength. In the context of the invention the strength of a substantially spherical core particle may suitably be determined as the ratio between the force required to initiate crushing of the particle under the test conditions as specified below (vide infra), and the square of the core diameter (i.e. regarding the particle as being substantially spherical).

It is preferable that the mean value of this ratio, determined for a representative number of cores (suitably ≧20 cores) taken at random from a bulk quantity of cores, is greater than 400 g/mm$^2$, more preferably greater than 600 g/mm$^2$, such as greater than 800 g/mm$^2$. It is especially desirable that the ratio in question is greater than 1000 g/mm$^2$, more preferably greater than 1200 g/mm$^2$, in particular greater than 1400 g/mm$^2$, and most preferably greater than 1600 g/mm$^2$.

The principle of a crushing test suitable for measuring the strength of a core particle (or a finished enzyme-containing granule) in the context of the present invention is illustrated in FIG. 1 herein (vide infra). The test is performed as follows:

1) A particle of core material is placed between an aluminium plate and a Plexiglas™ [transparent poly (methyl methacrylate)-type polymer] plate (each plate measuring 218 mm×40 mm, thickness 3.2 mm) as shown in FIG. 1; the Plexiglas™ plate is strengthened by two aluminium U-profiles attached to the edges of the plate [as indicated in the "front view" (end view) at the bottom of FIG. 1] and extending along the full length of the plate;

2) increasing loads (circular/cylindrical weights) are placed successively on the end of the Plexiglas™ plate, closest to the core, as shown in FIG. 1, such that the center of mass of the weight is positioned in the middle of the width of the plate, and 20 mm from the end thereof; at the same time, the particle is observed through the transparent plate by means of a microscope;

3) the loading (in grams) at which crushing of the particle begins (as assessed visually) is measured, and is divided by the square of the diameter of the core particle (in mm$^2$) to obtain the strength of the core particle.

Alternatively, the physical strength of particles of core material (or of granules according to the invention) can be measured according to either the Heubach method or the Novo Nordisk attrition method, both of which give a measure of the dust-formation tendency of particles; protocols for the latter two methods (EAL-SM-0289.01/01 and AF 225/2-GB, respectively) are obtainable on request from Novo Nordisk A/S, Bagsvaerd, Denmark. In both of the latter methods a bed of particles is subjected to the action of rolling steel balls, with simultaneous suction of air through the bed to collect dust and fragments created during the process.

For numerous applications of enzyme-containing granules of the invention, the mean particle size of the granules (and in many cases, correspondingly, of the core particles therein) will suitably be in the range from 50 to 4000 μm, such as 200–2000 μm (e.g. in the range of 200–1000 μm). The optimal mean core particle size will generally depend on the intended use of the final enzyme-containing granulate.

Embodiments of enzyme-containing granulates of the invention are well suited for use, for example, in detergents, in animal feed compositions, in baking and in the treatment of textiles. By way of example, for detergent applications the preferred mean granule particle size (and, in many cases, the corresponding mean core particle size) will often be in the range of 250–2000 μm (such as 300–2000 μm), whereas for baking applications the preferred mean core particle size will often be in the range of 50–200 μm. Granules (and, correspondingly, often cores) of a size greater than 4000 μm, such as particles of size of the order of 10000 μm, may be appropriate for certain applications (e.g. in the treatment of textiles).

The overall particle size distribution is preferably relatively narrow, e.g. such that for at least 90%, more preferably 95%, of the particles in a given sample the ratio between the largest and the smallest particle size is less than 4:1, preferably less than 3:1, more preferably less than 2:1, and most preferably less than 1.5:1.

Granular core particles suitable as the basis for enzyme-containing granules in accordance with the present invention may be prepared, e.g., by conventional granulation methods such as tumbling, rolling, pelletization, extrusion/-spheroidization, and/or mechanical agitation of the starting material, e.g. starting material comprising starch or a silicate/siliceous material. Examples of suitable absorbent cores ("placebo T" cores) which may be prepared by drum granulation (in the manner disclosed in U.S. Pat. No. 4,106, 991) are described above (see also Examples 8 and 13 herein).

Coating layers

The granules of the present invention may comprise one, two or more coating layers. Such coating layers may, for example, be one or more intermediate coating layers, or one or more outside coating layers, or a combination thereof.

Coating layers may perform any of a number of functions in a granule composition, depending on the intended use of the enzyme granule. Thus, for example, a coating may achieve one or more of the following effects:

(i) further reduction of the dust-formation tendency of an uncoated granule according to the invention;

(ii) protection of enzyme(s) in the granule against oxidation by bleaching substances/systems (e.g. perborates, percarbonates, organic peracids and the like);

(iii) dissolution at a desired rate upon introduction of the granule into a liquid medium (such as an aqueous medium);

(iv) provision of a barrier against ambient moisture in order to enhance the storage stability of the enzyme and reduce the possibility of microbial growth within the granule.

In appropriate embodiments of granules according to the present invention, the coating layer may be composed as described in U.S. Pat. No. 4,106,991 [e.g. with a waxy material such as polyethylene glycol (PEG), optionally followed by powdering with a whitener such as titanium dioxide].

A given coating layer may contribute from 0.5% to as much as 50% by weight of the finished granule.

Coating layers in/on granules of the present invention may further comprise one or more of the following: antioxidants, chlorine scavengers, plasticizers, pigments, lubricants (such as surfactants or antistatic agents) and additional enzymes.

Plasticizers useful in coating layers in the context of the present invention include, for example: polyols such as sugars, sugar alcohols, or polyethylene glycols (PEGs) having a molecular weight less than 1000; urea, phthalate esters such as dibutyl or dimethyl phthalate; and water.

Suitable pigments include, but are not limited to, finely divided whiteners, such as titanium dioxide or kaolin, coloured pigments, water soluble colorants, as well as combinations of one or more pigments and water soluble colorants.

As used in the present context, the term "lubricant" refers to any agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents.

Examples of suitable lubricants are polyethylene glycols (PEGs) and ethoxylated fatty alcohols.

As already mentioned, the present invention also relates to a process for producing enzyme-containing granules from absorbent cores, the process comprising:

(a) contacting absorbent cores, capable of absorbing at least 5% w/w (based on the weight of the core) of water, with a liquid medium containing an enzyme in dissolved and/or dispersed form, the amount of the liquid medium employed being such that substantially no attendant agglomeration of the resulting product occurs; and (b) at least partially removing volatile components of the liquid medium from the resulting product.

Preferred characteristics of cores suitable for use in the process of the invention are those already discussed above in connection with enzyme-containing granules of the invention.

In the process of the invention, the contacting of the absorbent cores with a liquid medium (such as an aqueous medium) comprising dissolved and/or dispersed enzyme is suitably carried out, for example, by spraying the cores with the solution/dispersion under mixing conditions, or by applying (e.g. by spraying) the enzyme solution/dispersion to cores which are fluidized (e.g. in a fluid-bed apparatus), or by a combination of both techniques.

Contacting of cores with enzyme via a mixing technique is generally well suited in the context of the invention, since it facilitates—when appropriate—addition, in step (a) of the process of the invention, of the enzyme-containing solution or dispersion to the cores in an amount, and for a period of time, which is sufficient to wholly (or partly) exploit the absorption capacity of the cores, but which does not leave any significant amount of free liquid phase (i.e. enzyme-containing solution or dispersion) on or between the resulting individual particles, i.e. such that there is insufficient free (unabsorbed) liquid phase to cause agglomeration of the particles to occur. If surplus (unabsorbed) liquid phase is present there is a risk of agglomeration occurring, with attendant unwanted formation of lumps in the bulk granulate.

Conventional mixing equipment can satisfactorily be used to mix the cores with the enzyme-containing liquid medium. The mixing equipment can be a batch mixer or a continuous mixer, such as a convective mixer [see, e.g., Hamby et al., *Mixing in the Process Industries*, pp. 39–53 (ISBN 0-408-11574-2)]. Non-convective mixing equipment, e.g. rotating drum mixers or so-called pan-granulators, may also be employed.

As already indicated, conditions whereby the cores are fluidized (such as in a fluid-bed apparatus or other form of fluidizing equipment, such as a Huttlin-type fluidizer) may also be employed when contacting the cores and the enzyme-containing liquid medium. For a description of suitable fluid-bed equipment, see, e.g., Hamby et al., *Mixing in the Process Industries*, pp. 54–77 (ISBN 0-408-11574-2).

In general, it is advantageous that the enzyme-containing liquid medium employed in the process of the invention contains dissolved enzyme. This will normally be the case when working with aqueous media. It is further desirable that the process is carried out under conditions such that absorption of the liquid phase (which will often contain dissolved enzyme) of the liquid medium by the cores takes place to some extent in step (a) of the process, often preferably to an extent such that essentially complete absorption of the liquid phase by the cores takes place before taking any measures to remove volatile components of the liquid medium from the resulting product.

In this connection, the process of the invention may thus be performed, for example, under conditions whereby essentially no removal, or at least very little removal, of volatile components takes place during the contacting phase. When using a mixer set-up in the contacting step, this may generally be achieved by simply ensuring that temperature in the mixer is not too high (e.g. such that the temperature is ambient temperature or below); when using fluidized conditions in the contacting step, this condition may generally be met by employing fluidizing air of sufficiently low temperature (e.g. a temperature below 30° C., such as ambient temperature or below).

Volatile components may subsequently be removed, for example, in a mixer, under mixing conditions (e.g. by applying heat and/or reduced pressure) or under fluidized conditions, e.g. in a fluid-bed apparatus (for example by the application of suitably hot fluidizing air). The temperatures employed should, of course, be such that no significant loss of enzyme activity of the product granules occurs.

Alternatively, some degree of evaporation of volatile components may be allowed to take place simultaneously with the performance of the contacting step. Thus, for example, when employing a mixer set-up in the contacting step, the mixer may be heated to a moderately elevated temperature in order to cause some evaporation of volatiles during the contacting stage; when employing fluidized conditions in the contacting step, the fluidizing air itself may be heated to a moderately elevated temperature. As before, the temperatures employed should, of course, be such that no significant loss of enzyme activity of the product granules occurs.

When drying product granules, they may suitably be retained in the process apparatus for a period of time sufficient to reduce the moisture content (in the case of products prepared using an aqueous, enzyme-containing medium) to a level below 10% w/w free moisture, preferably below 5% w/w free moisture.

As already discussed (vide supra), cores employed in the context of the invention are intrinsically able to absorb suitable amounts of water (and thereby of aqueous media), and consequently there is no need to include a surfactant in the enzyme-containing liquid medium in order for the cores to be able to absorb a sufficient amount of a hydrophilic polypeptide such as an enzyme.

This is particularly advantageous with respect to the production of enzyme-containing granulates for use in industries such as the baking industry or the animal feed industry, where the presence of surfactant in the granules is generally undesirable.

Nevertheless, in certain situations, such as when a product of higher enzymatic activity than usual is required (e.g. for use in the detergent industry), it may be advantageous, at least for certain types of absorbent core, to include an appropriate amount of surfactant in the enzyme-containing liquid medium for the purpose of enhancing and/or accelerating absorption of enzyme by the core. Surfactants suitable for this purpose include numerous types of cationic, anionic, non-ionic or zwitterionic surfactants, and suitable examples hereof are mentioned below, in connection with the discussion of detergent compositions (vide infra).

In order to promote formation of a dense, compact (smooth/regular) granule surface after contacting the cores with the enzyme-containing liquid phase, the presence in the mixer of a rapidly rotating granulating device ("choppers") is preferable. Reference may be made to U.S. Pat. No. 4,106,991 for further details.

Another way in which to promote the formation of a dense, compact (smooth/regular) surface after contacting the cores with the liquid medium is to treat the moist granulate in a Marumerizer™. Reference may be made to U.S. Pat. No. 4,106,991 for further details.

When an aqueous, enzyme-containing solution/dispersion is employed in accordance with the invention, the solution (i.e. the liquid phase of the aqueous medium) will normally preferably have a dry matter content of from 2% w/w to 50% w/w [dry matter consisting of enzyme protein(s), possibly together with other organic and inorganic materials]. When dispersed enzyme is present, the solution/dispersion will suitably have a dry matter content of from 10% w/w to 70% w/w [including dry matter originating from both dissolved and dispersed (undissolved) material].

The term "dispersion" as used in this connection designates a system containing solid particles, at least some of which comprise or consist of enzyme, of a size from the colloidal size range and upwards, and which are suspended, slurried or otherwise distributed in a liquid phase (such as an aqueous phase). The term "dispersion" in the context of the invention thus embraces, inter alla, suspensions and slurries.

In a preferred aspect of the process of the invention, dispersed enzyme present in the liquid medium employed in step (a) comprises enzyme in crystalline form.

In the process of the invention it is preferable that the enzyme-containing liquid medium (solution or solution/-dispersion) is added to the particulate cores in a weight ratio (liquid medium:cores) of at least 0.05:1, more preferably at least 0.1:1, such as at least 0.15:1, for example at least 0.2:1, and often at least 0.5:1. The ratio employed will, in general, depend on the absorption capacity of the cores, and on the required strength of the final enzyme-containing granules.

One, two or more coating layers may be applied to the dried or partly dried, enzyme-containing granules by conventional methods, such as by pan-coating, mixer-coating, and/or fluid-bed coating. Suitable coatings/coating components include those already discussed above in connection with enzyme-containing granules of the invention.

Enzymes

Any enzyme or combination of different enzymes may be employed in the context of the present invention. Accordingly, when reference is made to "an enzyme" this will in general be understood include combinations of one or more enzymes.

The enzyme classification employed in the present specification with claims is in accordance with *Recommendations* (1992) *of the Nomenclature Committee of the International Union of Biochemistry and Molecular Biology*, Academic Press, Inc., 1992.

It is to be understood that enzyme variants (produced, for example, by recombinant techniques) are included within the meaning of the term "enzyme". Examples of such enzyme variants are disclosed, e.g., in EP 251,446 (Genencor), WO 91/00345 (Novo Nordisk A/S), EP 525,610 (Solvay) and WO 94/02618 (Gist-Brocades NV).

Types of enzymes which may appropriately be incorporated in granules of the invention include:

hydrolases [EC 3; such as lipases (EC 3.1.1.3) and other carboxylic ester hydrolases (EC 3.1.1); phytases, e.g. 3-phytases (EC 3.1.3.8) and 6-phytases (EC 3.1.3.26); α-amylases (EC 3.2.1.1) and other glycosidases (EC 3.2, which fall within a group denoted herein as "carbohydrases"); peptidases (EC 3.4, also known as proteases); and other carbonyl hydrolases];

oxidoreductases [EC 1; such as peroxidases (EC 1.11.1), laccases (EC 1.10.3.2) and glucose oxidases (EC 1.1.3.4)];

transferases (EC 2); isomerases (EC 5); and ligases (EC 6).

Examples of commercially available proteases (peptidases) include Esperase™, Alcalase™, Neutrase™, Durazym™, Savinase™, Pyrase™, Pancreatic Trypsin NOVO (PTN), Bio-Feed™ Pro and Clear-Lens™ Pro (all available from Novo Nordisk A/S, Bagsvaerd, Denmark).

Other commercially available proteases include Maxatase™, Maxacal™, Maxapem™, Opticlean™ and Purafect™ (available from Genencor International Inc. or Gist-Brocades).

Examples of commercially available lipases include Lipolase™, Lipolase™ Ultra, Lipozyme™, Palatase™, Novozym™ 435 and Lecitase™ (all available from Novo Nordisk A/S).

Other commercially available lipases include Lumafast™ (*Pseudomonas mendocina* lipase from Genencor International Inc.); Lipomax™ (Ps. pseudoalcaligenes lipase from Gist-Brocades/Genencor Int. Inc.; and Bacillus sp. lipase from Solvay enzymes. Further lipases are available from other suppliers.

In the present context, the term "carbohydrase" is used to denote not only enzymes capable of breaking down carbohydrate chains (e.g. starches) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): α-amylases (3.2.1.1), β-amylases (3.2.1.2), glucan 1,4-α-glucosidases (3.2.1.3), cellulases (3.2.1.4), endo-1,3(4)-β-glucanases (3.2.1.6), endo-1,4-β-xylanases (3.2.1.8), dextranases (3.2.1.11), chitinases (3.2.1.14), polygalacturonases (3.2.1.15), lysozymes (3.2.1.17), β-glucosidases (3.2.1.21), α-galactosidases (3.2.1.22), β-galactosidases (3.2.1.23), amylo-1,6-glucosidases (3.2.1.33), xylan 1,4-β-xylosidases (3.2.1.37), glucan endo-1,3-β-D-glucosidases (3.2.1.39), α-dextrin endo-1,6-α-glucosidases (3.2.1.41), sucrose a-glucosidases (3.2.1.48), glucan endo-1,3-α-glucosidases (3.2.1.59), glucan 1,4-β-glucosidases (3.2.1.74), glucan endo-1,6-β-glucosidases (3.2.1.75), arabinan endo-1,5-α-L-arabinosidases (3.2.1.99), lactases (3.2.1.108), chitosanases (3.2.1.132) and xylose isomerases (5.3.1.5).

Examples of commercially available carbohydrases include Alpha-Gal™, BioTFeed™ Alpha, Bio-Feed™ Beta, Bio-Feed™ Plus, Bio-Feed™ Plus, Novozyme™ 188, Celluclast™, Cellusoft™, Ceremyl™, Citrozym™, Denimax™, Dezyme™, Dextrozyme™, Finizym™, Fungamyl™, Gamanase™, Glucanex™, Lactozym™, Maltogenase™, Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novo Nordisk A/S). Further carbohydrases are available from other suppliers.

Examples of commercially available oxidoreductases (EC 1) include Gluzyme™ (enzyme available from Novo Nordisk A/S). Further oxidoreductases are available from other suppliers.

Suitable transferases (EC 2) in the context of the invention are transferases in any of the following sub-classes:

transferases transferring one-carbon groups (EC 2.1); transferases transferring aldehyde or ketone residues (EC 2.2); acyltransferases (EC 2.3); glycosyltransferases (EC 2.4); transferases transferring alkyl oraryl groups, other that methyl groups (EC 2.5); and transferases transferring nitrogeneous groups (EC 2.6).

A preferred type of transferase in the context of the invention is a transglutaminase (protein-glutamine γ-glutamyltransferase; EC 2.3.2.13).

Examples of transglutaminases are described in WO 96/06931 (Novo Nordisk A/S).

The amount of enzyme to be incorporated in a granule of the invention will depend on the intended use of the granulate. For many applications, the enzyme content will be as high as possible or practicable.

The content of enzyme (calculated as pure enzyme protein) in a granule of the invention will typically be in the range of from about 0.5% to 20% by weight of the enzyme-containing granule.

When, for example, a protease (peptidase) is incorporated in granules according to the invention, the enzyme activity (proteolytic activity) of the finished granules will typically be in the range of 1–20 KNPU/g. Likewise, in the case of, for example, a-amylases, an activity of 10–500 KNU/g will be typical, whilst for lipases, an activity in the range of 50–400 KLU/g will normally be suitable.

Other Adjunct Ingredients

Where appropriate, various additives (adjuncts) may be incorporated together with the enzyme in a granule of the invention. Relevant adjuncts agents may include: metal compounds (e.g. salts and/or complexes of transition metals), solubilizers, activators, anti-oxidants, dyes, inhibitors, binders, fragrances, enzyme-protecting agents/scavengers, such as ammonium sulphate, ammonium citrate, urea, guanidine hydrochloride, guanidine carbonate, guanidine sulphonate, thiourea dioxide, monoethanolamine, diethanolamine, triethanolamine, amino acids such as glycine, sodium glutamate and the like, proteins such as bovine serum albumin, casein, surfactants, including anionic surfactants, ampholytic surfactants, nonionic surfactants, cationic surfactants and long-chain fatty acid salts, builders, alkalis or inorganic electrolytes, bleaching agents, blueing agents and fluorescent dyes, and caking inhibitors. Reference may be made to WO 92/00384 for a description of appropriate surfactants.

Granules incorporating such adjuvants may be made by methods well known to those skilled in the art of enzyme granulation, including fluidized bed spray-coating, pan-coating and other techniques for building up a granule by adding consecutive layers on top of a starting core material.

In addition to the process, according to the invention, for the production of enzyme-containing granules as described above, the present invention further relates to enzyme-containing granules obtained by, or obtainable by, an embodiment of the process.

Applications of Enzyme-Containing Granules of the Invention

Granulates (enzyme-containing granules) according to the present invention can be used for a variety of industrial applications. Particulary interesting applications include their use in detergents, in animal feed compositions, in products for the baking industry and in textile-treatment products, and the following list indicates types of enzymes which are most typically of interest in each of these fields of application:

Detergents: proteases, amylases (e.g. α-amylases), cellulases, lipases, oxidoreductases;

Baking products: amyloglucosidases (glucoamylases, glucan 1,4-α-glucosidases), bacterial α-amylases, fungal α-amylases, maltogenic amylases, glucose oxidases, proteases, pentosanases;

Animal feed compositions: bacterial α-amylases, proteases, xylanases; phytases;

Textile-treatment products: cellulases, α-amylases.

In a further aspect, the invention thus relates to detergent compositions (especially laundry and dishwashing detergent compositions) comprising enzyme-containing granules according to, or produced in accordance with, the invention.

In yet another aspect, the invention encompasses animal feed compositions comprising enzyme-containing granules according to, or produced in accordance with, the invention.

A still further aspect relates to compositions for baking comprising enzyme-containing granules according to, or produced in accordance with, the invention.

Moreover, the invention also relates to the use of enzyme-containing granules according to, or produced in accordance with, the invention as an enzyme-containing component in:
- a detergent composition, e.g. for laundry washing or dishwashing;
- an animal feed composition;
- a composition for baking; or
- a composition for textile treatment (e.g. for colour clarification or for dyeing).

Detergent Compositions

According to the invention, the enzyme-containing granules of the invention may typically be a component of a detergent composition, e.g., a laundry detergent composition or a dishwashing detergent composition. As such, they may be included in the detergent composition in the form of an uncoated granulate or coated granulate coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591.

The detergent composition of the invention may be in any convenient form, e.g. as powder, granules or paste.

The detergent composition comprises one or more surfactants, each of which may be anionic, nonionic, cationic, oramphoteric (zwitterionic). The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

In addition to the enzymes contained in the enzyme-containing granules of the invention, the detergent composition may additionally comprise one or more other enzymes, such as a pullulanase, esterase, lipase, cutinase, protease, cellulase, amylase, peroxidase or oxidase (e.g. a laccase).

Normally the detergent contains 1–65% of a detergent builder, but some dishwashing detergents may contain even up to 90% of a detergent builder, or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates.

The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, polymaleates, maleic/acrylic acid copolymers and lauryl methacrylate/acrylic acid copolymers.

The detergent composition may contain bleaching agents of the chlorine/bromine-type or the oxygen-type. The bleaching agents may be coated or incapsulated. Examples of inorganic chlorine/bromine-type bleaches are lithium, sodium or calcium hypochlorite or hypobromite as well as chlorinated trisodium phosphate. The bleaching system may also comprise a $H_2O_2$ source such as perborate or percarbonate which may be combined with a peracid-forming bleach activator such as tetraacetylethylenediamine (TAED) or nonanoyloxybenzenesulfonate (NOBS).

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

In dishwashing detergents the oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED or NOBS.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type as described in EP 0 544 777 B1.

The detergent may also contain other conventional detergent ingredients such as, e.g., fabric conditioners including clays, deflocculant material, foam boosters/foam depressors (in dishwashing detergents foam depressors), suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

Particular forms of laundry detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O,2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO) or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O,2SiO_2$) | 3–9% |
| Zeolite (as $NaAlSiO_4$) | 23–33% |
| Sodium sulfate (as $NaSO4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

6) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

7) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

8) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |

| | |
|---|---|
| Soluble silicates (as Na$_2$O, 2SiO$_2$) | 5–15% |
| Sodium sulfate (as Na$_2$SO$_4$) | 0–5% |
| Zeolite (as NaAlSiO$_4$) | 15–28% |
| Sodium perborate (as NaBO$_3$.4H$_2$O) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

9) Detergent formulations as described in 1)-8) wherein all or part of the linear alkylbenzenesulfonate is replaced by (C$_{12}$–C$_{18}$) alkyl sulfate.

10) A detergent composition formulated as a granulate having a bulk density of at least 600 g/l comprising

| | |
|---|---|
| (C$_{12}$–C$_{18}$) alkyl sulfate | 9–15% |
| Alcohol ethoxylate | 3–6% |
| Polyhydroxy alkyl fatty acid amide | 1–5% |
| Zeolite (as NaAlSiO$_4$) | 10–20% |
| Layered disilicate (e.g. SK56 from Hoechst) | 10–20% |
| Sodium carbonate (as Na$_2$CO$_3$) | 3–12% |
| Soluble silicate (as Na$_2$O,2SiO$_2$) | 0–6% |
| Sodium citrate | 4–8% |
| Sodium percarbonate | 13–22% |
| TAED | 3–8% |
| Polymers (e.g. polycarboxylates and PVP) | 0–5% |
| Enzymes (calculated as pure enzyme protein) | 0.0001–0.1% |
| Minor ingredients (e.g. optical brightener, photo bleach, perfume, suds suppressors) | 0–5% |

11) A detergent composition formulated as a granulate having a bulk density of at least 600 g/l comprising

| | |
|---|---|
| (C$_{12}$–C$_{18}$) alkyl sulfate | 4–8% |
| Alcohol ethoxylate | 11–15% |
| Soap | 1–4% |
| Zeolite MAP or zeolite A | 35–45% |
| Sodium carbonate (as Na$_2$CO$_3$) | 2–8% |
| Soluble silicate (as Na$_2$O,2SiO$_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

12) Detergent formulations as described in 1)–11) which contain a stabilized or encapsulated peracid, either as an additional component or as a substitute for already specified bleach systems.

13) Detergent compositions as described in 1), 3), 5), 7) and 8) wherein perborate is replaced by percarbonate.

14) Detergent compositions as described in 1), 3), 5), 7), 8), 10) and 11) which additionally contain a manganese catalyst. The manganese catalyst may, e.g., be one of the compounds described in "Efficient manganese catalysts for low-temperature bleaching", *Nature* 369, 1994, pp. 637–639.

Particular forms of dishwashing detergent compositions within the scope of the invention include:

1) Powder Automatic Dishwashing Composition

| | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetylethylenediamine (TAED) | 1–4% |
| Sodium sulphate | 5–33% |
| Enzymes | 0.0001–0.1% |

2) Powder Automatic Dishwashing Composition

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetylethylenediamine (TAED) | 1–2% |
| Polyacrylate polymer (e.g. maleic acid/acrylic acid copolymer) | 6–25% |
| Enzymes | 0.0001–0.1% |
| Perfume | 0.1–0.5% |
| Water | 5–10 |

3) Powder Automatic Dishwashing Composition

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetylethylenediamine (TAED) | 0–6% |
| Maleic acid/acrylic acid copolymer | 0–5% |
| Clay | 1–3% |
| Poly (amino acids) | 0–20% |
| Sodium polyacrylate | 0–8% |
| Enzymes | 0.0001–0.1% |

4) Powder Automatic Dishwashing Composition

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetylethylenediamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

5) Powder Automatic Dishwashing Composition

| | |
|---|---|
| Nonionic surfactant | 1–7% |
| Sodium disilicate | 18–30% |
| Trisodium citrate | 10–24% |

-continued

| | |
|---|---|
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylenetriaminepentaacetate, pentasodium salt | 0–2.5% |
| Enzymes | 0.0001–0.1% |
| Sodium sulphate, water | Balance |

6) Automatic dishwashing compositions as described in 1), 2), 3) and 4), wherein perborate is replaced by percarbonate.

7) Automatic dishwashing compositions as described in 1)–4) which additionally contain a manganese catalyst. The manganese catalyst may, e.g., be one of the compounds described in "Efficient manganese catalysts for low-temperature bleaching", Nature 369, 1994, pp.637–639.

All of the particular forms of washing and dishwashing detergent compositions listed above will, of course, additionally comprise minor amounts of granulate constituents (core material, coating constituents, etc.)

The enzyme-containing granules of the invention may be incorporated in concentrations corresponding to enzyme concentrations conventionally employed in detergents. It is at present contemplated that, in a detergent composition of the invention, the enzymes may be added in an amount corresponding to 0.00001–1 mg (calculated as pure enzyme protein) of enzyme per liter of wash/dishwash liquor.

Reference is made to WO 97/07202 (PCT/DK96/00341) for details concerning further types of detergent compositions relevant in the context of the present invention.

The present invention is further illustrated by the working examples described below, which are representative and are not intended to limit the scope of the invention in anyway. One skilled in the art will be capable of selecting other enzymes, cores, coating agents/adjuvants or methods on the basis of the teaching herein.

MATERIALS AND METHODS

Enzyme Activity Assays

Proteolytic Activity (KNPU): In the present specification, proteolytic activity is expressed in Kilo Novo Protease Units (KNPU). The activity is determined relative to an enzyme standard, and the determination is based on the digestion of a dimethyl-casein (DMC) solution by the proteolytic enzyme under standard conditions (50° C., pH 8.3, 9 min. reaction time, 3 min. measurement time). A brochure (AF 220/1) providing further details of the analytical method is available upon request from Novo Nordisk A/S, Bagsvaerd, Denmark.

Amylolytic activity (KNU) may be determined using potato starch as substrate. This method is based on the hydrolysis of modified potato starch by the enzyme, and the reaction is followed by mixing samples of the starch/enzyme solution with an iodine solution. Initially, a blackish-blue colour is formed, but during the breakdown of the starch the blue colour becomes weaker and gradually changes to a reddish-brown, which is compared to a coloured glass standard. One Kilo Novo alpha Amylase Unit (KNU) is defined as the amount of enzyme which, under standard conditions (37±0.05° C., 0.0003 M $Ca^{2+}$, pH 5.6) dextrinizes 5.26 g starch dry substance Merck Amylum solubile.

A brochure (AF 9/6) describing this analytical method in more detail is available upon request from Novo Nordisk A/S, Denmark.

Lipolytic activity (LU) may be determined using tributyrin as substrate. This method is based on the hydrolysis of tributyrin catalyzed by the enzyme, and the consumption of alkali is measured as a function of time. One Lipase Unit (LU) is defined as the amount of enzyme which, under standard conditions (30.0° C., pH 7.0; Gum Arabic as emulsifier and tributyrin as substrate) liberates 1 mmol of titratable butyric acid per minute. A brochure (AF 95/5) describing this analytical method in more detail is available upon request from Novo Nordisk A/S, Denmark.

Phytase activity (FYT) may be determined using Novo Nordisk analytical method KAL-SM-0403.01/01 (available upon request from Novo Nordisk A/S, Denmark).

Cores

Cassava starch cores: If nothing else is stated, cassava starch cores employed were obtained from Agro Comercial, Brazil.

Nonpareil cores (sugar-starch based): obtained from Crompton & Knowles, USA ("Sugar Spheres NF Mesh 35–40") or from NP Pharma.

Enzymes

Savinase™ concentrate (water-based protease concentrate) was obtained from Novo Nordisk A/S, Denmark.

Phytase concentrate was obtained from Novo Nordisk A/S, Denmark.

Lipase (lipase variant HL9) was obtained as described in Example 3 of WO 97/07202.

Heubach method and Novo Nordisk attrition method

As already mentioned (vide supra), both the Heubach method and the Novo Nordisk attrition method are methods wherein a bed of granules is exposed to the action of rolling steel balls with simultaneous suction of air through the bed to collect dust and fragments created during the process. Brochures (EAL-SM-0289.01/01 and AF 225/2-GB, respectively) describing these methods in more detail are available upon request from Novo Nordisk A/S, Denmark.

EXAMPLE 1

A 15 kg portion of granular cassava starch cores (particle size distribution: 97% of the material between 0.5 mm and 1.0 mm in diameter) was introduced into a 50 liter Lödige mixer and sprayed, with mixing by means of the mixing blades ("ploughshares"), with a total of 6.0 kg of pure water (40% w/w relative to the cores), initially by spraying on 3.5 kg of water without operating the "chopper" (compacting knives) and then by spraying on the remaining amount of water (2.5 kg), while operating the chopper, up the total amount of 6.0 kg.

The wetted cores were inspected regularly during the spraying and showed no sign of stickiness or tendency towards agglomeration which could cause problems during subsequent drying or problems with respect to the quality of the final product.

The resulting product was transferred to a Glatt WSG 15 fluid-bed apparatus (Glatt, Germany) with an air-inlet temperature of 62° C., and dried for 30 minutes, or until the product temperature exceeded 50° C., and then sieved on a 1.2 mm mesh screen, leaving only 0.8% w/w of residual, oversized particles on the sieve.

EXAMPLE 2

(Comparative Example Using a Poorly Absorbing Core)

A 15 kg portion of sugar-starch nonpareil cores was introduced into a 50 liter Lödige mixer and sprayed, with mixing by means of the mixing blades, stepwise with a total of 0.9 kg of water, starting with 0.3 kg.

The wetted cores were inspected regularly during the spraying. After spraying of the first 0.3 kg of water (2% w/w relative to the cores) the cores showed stickiness. By the time a total of 4–5% w/w of water had been sprayed on, stickiness was severe.

After spraying a total of 0.9 kg of water (6% w/w relative to the cores) the wetted cores were transferred to a Glatt WSG 15 fluid-bed apparatus for drying under the same conditions as in Example 1. However, even when attempts were made to mix the bed of wetted cores manually in the fluid-bed apparatus, the material proved to be too sticky to fluidize satisfactorily. The final dried product consisted mainly of agglomerated lumps or crusts with dimensions of up to about 10 cm.

This example demonstrates that the nonpareil cores in question are capable of absorbing less than 4% w/w of water.

EXAMPLE 3

Step 1: A 20 kg portion of granular cassava starch cores (as employed in Example 1; particle size distribution: 97% of the material between 0.5 and 1.0 mm in diameter) was introduced into a 50 liter Lödige mixer equipped with a multiple chopper head, where they were sprayed, with mixing by means of the mixing blades, with 4.5 kg of water-based, ultrafiltered liquid Savinase™ concentrate (33 KNPU/g). The Savinase™ concentrate was applied using a pressure nozzle submerged in the cores and spraying directly into the chopper. The mixing blades and the chopper were operated continuously during the spraying.

After applying the Savinase™ concentrate, the resulting granules were transferred to a Glatt WSG 5 fluid-bed apparatus and dried as described in Example 1.

Step 2: A 15 kg portion of the dried granulate was subsequently coated in the fluid-bed apparatus with 8% w/w of ammonium sulphate, using a 38% w/w ammonium sulphate solution and employing a conventional top spray coating technique (air inlet temperature 62° C., product temperature 43° C., spray rate 100 g/min, air flow 700 m$^3$/h).

Step 3: The ammonium sulphate coated granulate was further coated with 18.5% w/w of a coating of composition 27% TiO$_2$, 27% kaolin, 30% Glascol™ LS27 and 16% PEG 4000, using the same fluid bed top spray coating technique. The composition of the coating liquid was:

0.75 kg TiO$_2$ (Kronos™ 2044)

0.75 kg kaolin (Speswhite™ from English China Clay)

1.80 kg Glasco™ LS27 (from Allied Colloids Ltd., England; 46% dry matter)

0.45 kg Polyethylene glycol 4000 (PEG 4000)

2.40 kg water.

Step 4: Finally a surface coating of 0.75% w/w of PEG 4000 was applied using a 23% w/w water-based solution of PEG 4000 and employing the same fluid bed top spray technique as before.

The activity of the final granulate product after step 4 was 4.1 KNPU/g.

The dust-formation/physical strength properties of the granulate after step 1 and step 2 were evaluated according to the Novo Nordisk attrition method, whilst the products resulting from step 3 and step 4 were evaluated according to the Heubach method.

Dust Content After:

| | | |
|---|---|---|
| Step 1: Total dust 0.4 mg; | active dust | 2410 µg |
| Step 2: Total dust 0.5 mg; | active dust | 74 µg |
| Step 3: Total dust 6.2 mg; | active dust | 43 µg |
| Step 4: Total dust 0.0 mg; | active dust | <10 µg |

The amount of active dust is expressed as micrograms (µg) of a standard with an activity of 4.0 KNPU/g.

EXAMPLE 4

Step 1: A 15 kg portion of granular cassava starch cores (as employed in Example 1 and Example 3) was introduced into a 50 liter Lödige mixer, and sprayed, with mixing by means of the mixing blades, with 5.9 kg of liquid Savinase™ concentrate (33 KNPU/g) and dried as described in Example 1.

Steps 2–4: A 15 kg portion of the dried granulate from step 1 was treated as described in steps 2–4 in Example 3.

The activity of the final granulate product after step 4 was 10.0 KNPU/g The dust-formation properties of the products of steps 1–4 (determined as in Example 3) were as follows:

| | | |
|---|---|---|
| Step 1: Total dust 5.9 mg; | active dust | 7330 µg |
| Step 2: Total dust 0.0 mg; | active dust | 78 µg |
| Step 3: Total dust 2.6 mg; | active dust | <10 µg |
| Step 4: Total dust 0.0 mg; | active dust | <10 µg |

EXAMPLE 5

A 15 kg portion of granular cassava starch cores (as employed in Example 1) was introduced into a 50 liter Lödige mixer and sprayed, with mixing by means of the mixing blades, with 5.9 kg of liquid Savinase™ concentrate (18 KNPU/g) using a pneumatic nozzle placed in the funnel above the mixer. In this example the chopper was not operated during the spraying, but the sprayed granulate was subjected to treatment with the chopper for 3 minutes after the spraying.

The activity of the resulting granulate (uncoated granulate) was 6.28 KNPU/g, and the dust-formation properties of the product (determined by the Novo Nordisk attrition method) were as follows:

Total dust 0.5 mg; active dust 483 µg.

EXAMPLE 6

Comparative Example Using Poorly Absorbing Cores

In experiments using nonpareil cores (sugar-starch cores) sprayed successively with increasing amounts of liquid Savinase™ concentrate in the same manner as described in Examples 3, 4 and 5, the presence of surplus concentrate on the outer surface of the cores, with attendant particle agglomeration, was observed when ≧4% w/w (relative to the cores) of concentrate was applied.

This demonstrates that the nonpareil cores in question are able to absorb less than 4% w/w of the Savinase™ concentrate.

EXAMPLE 7

This example is a comparative example in which poorly absorbing, nonpareil (sugar-starch) cores are sprayed with an aqueous, enzyme-containing medium, and dried, in a conventional fluid-bed apparatus.

Step 1: A 15 kg portion of nonpareil cores (particle size distribution: 99% between 425 µm and 600 µm in diameter) was introduced into a Glaft WSG 5 fluid-bed apparatus and sprayed, under fluidized conditions, with a mixture of 4.0 kg of liquid Savinase™ concentrate (33 KNPU/g), 225 g of 20% Kollidon™ VA64 and 50 g of $TiO_2$ using a conventional top spray coating technique (inlet air temperature 65° C.; product temperature 42° C.;, spraying rate 100 g/minute; air flow 550 m³/hour).

The product was then fluid-bed dried as described above.

Steps 2–4: The product from step 1 was treated successively as in steps 2–4 in Example 3.

The activity of the final product was 6.2 KNPU/g.

The dust-formation properties of the various products (determined using the Novo Nordisk attrition method for the products from step 1 and step 2, and the Heubach method for the products from step 3 and step 4) were as follows:

| Step 1: Total dust 9.1 mg; active dust | 56900 µg |
| Step 2: Total dust 23.2 mg; active dust | 72400 µg |
| Step 3: Total dust 12.3 mg; active dust | 6660 µg |
| Step 4: Total dust 1.8 mg; active dust | 1570 µg |

It is apparent from these results that irrespective of the level of coating, the various products—based on poorly absorbent nonpareil cores—exhibit unfavourable dust-formation properties.

EXAMPLE 8

18 kg of a powder composition prepared from the following:

4.5 kg of fibrous cellulose (Arbocel™ FTC200), 3.0 kg of kaolin (Speswhite™, English China Clay) and 20.5 kg of finely ground sodium sulphate were sprayed with 9.5 kg of a 21% w/w aqueous solution of carbohydrate binder (Glucidex™ 21D, from Roquette Freres) and granulated and dried as described in Example 1 in U.S. Pat. No. 4,106,991.

The dry granulate was sieved, and the size fraction between 0.3 and 1.0 mm was used as enzyme-absorbing core in the following:

Step 1: A 18.5 kg portion of the core material was transferred to a 50 liter Lödige mixer and sprayed, with mixing by means of the mixing blades, with 4.5 kg of liquid Savinase™ concentrate. The product was dried as described in Example 3.

Steps 2–4: 16 kg of granulate from step 1 was transferred to a Glatt WSG5 fluid bed apparatus, and then dried as described above and treated further as described in steps 2–4 in Example 3.

The activity of the final product was 5.5 KNPU/g.

Dust-formation properties (determined using the Novo Nordisk attrition method for the products from step 1 and step 2, and the Heubach method for the products from step 3 and step 4) were as follows:

| Step 1: Total dust 11.6 mg; | active dust | 29900 µg |
| Step 2: Total dust 0.7 mg; | active dust | 741 µg |
| Step 3: Total dust 7.3 mg; | active dust | 367 µg |
| Step 4: Total dust 0.6 mg; | active dust | 51 µg |

EXAMPLE 9

Step 1: A 15 kg portion of granular cassava starch cores (as employed in Example 1) was introduced into a 50 liter Lödige mixer equipped with a multiple chopper head, where they were sprayed, with mixing by means of the mixing blades, with 5.0 kg of ultrafiltered Savinase™ concentrate (27.4 KNPU/g). The concentrate was sprayed into the cores as described in Example 3.

After applying the Savinase™ concentrate, the resulting granular material was transferred to a Glaft WSG 15 fluid-bed apparatus and dried as described above.

Step, 2: After drying, the resulting granulate was coated with a thin film coating (2% w/w in total) using a Wurster-type fluid-bed apparatus: 15 kg of the granulate from step 1 was transferred to a Glatt GRPC 15 fluid-bed apparatus (bottom spray) where it was sprayed with a mixture of 150 g of methylhydroxypropyl cellulose (Aqualon™ 8MP5C) and 150 g of PEG 4000 dissolved in 1.8 liters of water. Air inlet temperature: 55° C.; product temperature: 39.5° C. After spraying, the granulate was dried for 5 minutes and then cooled to 30° C.

The activity after the final step 2 was 7.0 KNPU/g.

Dust content after:

| Step 1: | Total dust 0.2 mg; Active dust 263 µg (Nova Nordisk attrition method) |
| Step 2: | Total dust 0.0 mg; Active dust 26 µg (Heubach method) |

These very low dust figures clearly demonstrate the physical quality of the enzyme/cassava core granulate, since only a thin film coating had been applied.

EXAMPLE 10

Step 1: A 15 kg portion of cassava starch cores (as employed in Example 1) was introduced into a Glatt WSG 5 fluid-bed apparatus and sprayed with a mixture consisting of 3.9 kg of liquid Savinase™ concentrate (27.4 KNPU/g), 200 g of a 20% w/w solution of Kollidon™ VA64 in water, and 50 g of $TiO_2$, as described in Example 7, step 1.

Step 2–4: The product was treated (coated) as described in Examples 3 and 7, steps 2–4.

The activity of the final product was 5.9 KNPU/g.

The dust-formation properties of the products of steps 1–4 (determined as in Example 3) were as follows:

| Step 1: Total dust 0.0 mg; | active dust 474 µg |
| Step 2: Total dust 1.7 mg; | active dust 1550 µg |
| Step 3: Total dust 3.3 mg; | active dust 294 µg |
| Step 4: Total dust 0.0 mg; | active dust <10 µg |

This example demonstrates that the contacting/absorption of step (a) of the process according to the invention may be performed in a fluid-bed and still yield a product exhibiting excellent properties (such as low dust formation). In contrast, the similar procedure described in Example 7 (vide supra), using a poorly absorbing non-pareil core, gave products exhibiting relatively high dust levels.

In addition to absorption properties, a combination of one or more of factors such as high physical strength, high degree of sphericity, smoothness and degree of starch gelatinization of the absorbent cores in question is believed to contribute to the low dust figures observed for products (products according to the invention) exemplified by those obtained in the present example, and in other examples herein (e.g. Example 3), which employ cores of a type preferred in the context of the invention.

EXAMPLE 11

In this example a liquid enzyme was partly absorbed into, partly layered onto, a cassava core, the entire process being carried out in a Huttlin-type fluidizer with bottom spray.

Step 1: A 3.5 kg portion of cassava starch cores (as employed in Example 1) was introduced into a 5 liter Huttlin Turbojet fluidizer type HKC-5-TJ, where they were sprayed with 1500 g of liquid Savinase™ concentrate (27.4 KNPU/g), keeping the product temperature at 24° C. by slowly raising the inlet temperature from 35° C. to 65° C. At this point the granulate was too wet to fluidize properly, and it was consequently dried by stopping the spraying and allowing the product temperature to rise to 40° C. After drying, the product was sprayed with a further 1600 g of the Savinase™ concentrate (inlet air temperature 80° C.; product temperature 44° C.). After the spraying, the product was dried by continuing the passage of inlet air (80° C.) for 2 minutes, and then cooled.

Step 2: The dried granulate from step 1 was subsequently coated in the fluid-bed apparatus with 8% w/w of ammonium sulphate by spraying with a 38% w/w aqueous ammonium sulphate solution (inlet air temperature 78° C.; product temperature 38° C.).

Step 3: The ammonium sulphate coated granulate was further coated with 18.5% w/w of a coating with a composition as described in Example 3, step 3, the composition of the coating liquid employed being the same as employed in step 3 of Example 3.

Step 4: Finally a surface coating was applied as described in Example 3 step 4.

The activity of the final granulate after step 4 was 18.5 KNPU/g.

Dust-formation properties of the final product (Heubach method):

Total dust: 0.4 mg; active dust: 28 µg

The results demonstrate that the product (a product according to the invention which not only has enzyme absorbed within the core, but also has enzyme deposited on the outer surface thereof) obtained by this procedure (a process within the scope of the present invention) not only has a very high enzyme content (and thereby very high activity), but also exhibits very low tendency towards dust formation.

Without being bound to any theory, it is believed that the adherence of enzyme deposited on the outer surface of an absorbent core of the type of relevance in the context of the invention is enhanced by the presence, within the surface of the core, of absorbed enzyme, and thus that the tendency to dust formation by such a product is correspondingly reduced.

EXAMPLE 12

Step 1: A 15 kg portion of cassava starch cores (as employed in Example 1) was introduced into a 50 liter Lödige mixer equipped with a multiple chopper head, and the cores were sprayed, with mixing by means of the mixing blades, with a total of 5.0 kg of an ultrafiltered lipase concentrate with an activity of 145 KLU/g. The preparation of the lipase in question is described in WO 97/07202 (see Example 3, variant HL9, therein). The concentrate was sprayed from a two-fluid nozzle (air atomizer nozzle) placed in the funnel above the mixer.

After the lipase concentrate had been applied, the resulting granular material was transferred to a Glaft WSG 5 fluid-bed apparatus and dried as described previously, above.

Step 2: After drying, the resulting granulate was coated with 4.8% w/w of PEG 4000 and 12.5% w/w of a 1:1 mixture of titanium dioxide and kaolin, using a procedure as described in U.S. Pat. No. 4,106,991 (Example XXII therein), with the exception that PEG 4000 was used herein instead of PEG 1500.

The activity of the final granulate product after step 2 was 32 KLU/g.

EXAMPLE 13

This example describes the preparation of an enzyme-containing granulate of a known type (viz. a granulate in accordance with U.S. Pat. No. 4,106,991) for comparison purposes (see Example 14, below).

Step 1: A powder mixture with the following composition:

2.25 kg of fibrous cellulose (Arboce™ BFC200)

1.50 kg of kaolin (Speswhite™, from English China Clay)

1.00 kg of carbohydrate binder (Glucidex™ 21 D, Roquefte Freres)

9.35 kg of ground sodium sulphate was sprayed with 3.0 kg of Lipase concentrate (as employed in Example 12) in which was further dissolved 0.4 kg of carbohydrate binder (Glucidex™ 21D). The mixture was granulated and dried as described in U.S. Pat. No. 4,106,991 (Example 1 therein).

Step 2: The dry granulate was sieved to obtain a product with a particle size range of 0.3–1.2 mm; this product was subsequently coated as described in Example 12, step 2.

The activity of the final granulate product after step 2 was 20 KLU/g.

EXAMPLE 14

This example compares the storage stability in detergents of (i) a lipase-containing, starch-based granulate in accordance with the present invention (Example 12, above), and (ii) a lipase-containing granulate produced in accordance with U.S. Pat. No. 4,106,991 (Example 13, above).

A: Storage in a Perborate-Containing Detergent with TAED

Products produced according to Example 12 and Example 13, respectively, were mixed (to an enzyme content of ca. 1 KLU/g of detergent) into a traditional (non-compact), zeolite-built powder detergent containing sodium perborate and tetraacetylethylenediamine (TAED). Analytical results (residual lipase activity) obtained after storage of the resulting enzyme-containing detergent composition under various conditions are given in the tables below:

(i) Storage at 35° C. and 55% relative humidity in open jars

| Granulate | % residual activity (2 determinations) after | |
|---|---|---|
| | 2 weeks | 4 weeks |
| Example 12 | 93–96 | 101–105 |
| Example 13 | 80–84 | 78–71 |

(ii) Storage at 37° C. and 70% relative humidity in open jars

| Granulate | % residual activity after | | |
|---|---|---|---|
| | 3 days | 7 days | 14 days |
| Example 12 | 100 | 90 | 91–87 |
| Example 13 | 84 | 68 | 49–43 |

B: Storage in a Percarbonate-Containing Detergent

Products produced according to Example 12 and Example 13, respectively, were mixed (to an enzyme content of ca. 1 KLU/g of detergent) into a standard, compact, European-type powder detergent containing sodium percarbonate. Analytical results (residual lipase activity) obtained after storage of the resulting enzyme-containing detergent composition under specified conditions are given in the table below:

(i) Storage at 35° C. and 55% relative humidity in open jars

| Granulate | % residual activity after | |
|---|---|---|
| | 2 weeks | 4 weeks |
| Example 12 | 97–100 | 92–89 |
| Example 13 | 58–52 | 36–35 |

EXAMPLE 15

This example describes the preparation of absorbent cores (enzyme-free) of a type similar to those produced in Example 8, but containing rice starch instead of sodium sulphate.

A 14 kg portion of ground, recycled, enzyme-free cores (produced using the methodology of EP 0 304 331 B1, but without incorporating enzyme) with a composition corresponding to that of a mixture of the following amounts of the following powder components was mixed with the powder components in question, viz.

3.15 kg of fibrous cellulose (Arbocel™ BFC200)
2.10 kg of kaolin (Speswhite™, from English China Clay) and
12.75 kg of rice starch (from Remy Industri).

The dry mixture was sprayed with 14 kg of a 21.4% w/w solution of carbohydrate binder (Glucidex™ 21 D) in water, and granulated and dried as described in EP 0 304 331 B1 (Example 1 therein).

The dry granulate (cores) was sieved to obtain cores with a particle size in the range of 0.3–1.1 mm.

EXAMPLE 16

Step 1: A 15 kg portion of the sieved cores from Example 15 was sprayed with 3.3 kg of Savinase™ concentrate (33 KNPU/g) in a Lödige mixer as described in Example 3. The thus welted granulate was then powdered, in the mixer, with 300 g of kaolin (Speswhite™). The product was then transferred to a Marumerizer™ (from Fuji Paudal, Osaka, Japan), where it was further spheronized. The resulting granulate was dried in a Glatt WSG 5 fluid-bed apparatus essentially as in Example 1.

Steps 2–4: The dried granulate was coated as described in Example 3, steps 2–4.

The activity of the final granulate after step 4 was 4.7 KNPU/g.

Dust Content After:

| | |
|---|---|
| Step 1: Total dust 0.4 mg; (Novo Nordisk attrition method). | active dust 1000 μg |
| Step 2: Total dust 1.0 mg; (Novo Nordisk attrition method). | active dust 194 μg |
| Step 4: Total dust 0.6 mg; (Heubach method). | active dust <10 μg |

EXAMPLE 17

Step 1: A 15 kg portion of cassava starch cores (as employed in Example 1) in a 50 liter Lödige mixer was sprayed, with mixing by means of the mixing blades, with 5.0 kg of Savinase™ concentrate (33 KNPU/g) and dried as described in Example 3, with the exception that the spray nozzle did not spray directly into the chopper but from the funnel above the mixer.

Step 2: A 2.0 kg portion of dried granulate was transferred to a 5 liter Lödige mixer and coated with 3% w/w of PEG 4000 and 3% w/w of a 1:1 mixture of titanium dioxide and kaolin in a manner as described in U.S. Pat. No. 4,106,991 (Example XXII therein).

The final granulate had an activity of 10.8 KNPU/g and a dust content (according to the Heubach method) of 0.2 mg total dust and 37 μg active dust.

EXAMPLE 18

A granulate was prepared as described in Example 17, above, except that the final coating consisted of 5% w/w of PEG 4000 and 13% w/w of a 1:1 mixture of titanium dioxide and kaolin.

The product granulate had an activity of 10.5 KNPU/g, and had adust content(Heubach) of 0.4 mg total dust and <10 μg active dust.

By way of comparison, it may be mentioned that a granulate produced according to U.S. Pat. No. 4,106,991 and with a coating of the type described in the present example generally exhibits dust figures of around 200–300 μg active dust.

EXAMPLE 19

Enzyme-free cores (absorbent cores) of composition:
10.0% w/w of fibrous cellulose (Arbocel™ BC200)
10.0% w/w of kaolin (Speswhite™)
10.0% w/w of carbohydrate binder (3:2 mixture of Glucidex™ 21 D and Sorbitol) balance: sodium sulphate was produced, by a continuous procedure, according to U.S. Pat. No. 4,106,991, leading to cores which were not fully compacted and fully spheronized. These cores were compacted and physically improved in the following manner:

Step 1: An 18 kg portion of the (enzyme-free) cores was sprayed with 3.0 kg of Savinase™ concentrate (27.4 KNPU/ g), in which was dissolved 2% w/w of sodium thiosulphate, in a manner as described in Example 12, above.

After mixing the product for 2 minutes (operating both the mixer blades and the chopper), the granulate was powdered with 600 g of rice starch (Remy Industri), and then sprayed with a further 500 g of Savinase™ concentrate.

A further 600 g of rice starch was applied, followed by a further spraying with 500 g of Savinase™ concentrate.

Finally, the granulate was powdered with a further 600 g of rice starch, and then with 360 g of kaolin.

During all the latter procedures, the mixer blades and the chopper were operated in order to compact the granulate and smoothen the surface of the granules.

The granulate was then dried as described in Example 1.

Steps 2–3: A 15 kg portion of the dried granulate was coated as described in Example 3, steps 2–3.

The activity of the final product after step 3 was 6.4 KNPU/g.

Dust content (Heubach): total dust 0.1 mg; active dust 32 µg.

This example demonstrates that the tendency to dust formation by enzyme-containing granules (granules according to the invention) based on "placebo" cores (enzyme-free cores) prepared according to the methodology of U.S. Pat. No. 4,106,991 can be still further reduced by starch coating followed by application/absorption of enzyme.

EXAMPLE 20

Sphericity of Cassava Starch Cores

This example gives the results of measurements (by microscopy) of the sphericity, expressed as the ratio between the largest diameter ($d_{max}$) and the smallest diameter ($d_{min}$), for each of 20 cassava starch cores taken at random from a batch of cores (size distribution: 97% between 0.5 mm and 1.0 mm) supplied by Agro Comercial, Brazil.

The results were as follows:

| Particle No. | $d_{max}/d_{min}$ |
| --- | --- |
| 1 | 1.056 |
| 2 | 1.029 |
| 3 | 1.086 |
| 4 | 1.025 |
| 5 | 1.188 |
| 6 | 1.852 |
| 7 | 1.117 |
| 8 | 1.032 |
| 9 | 1.025 |
| 10 | 1.056 |
| 11 | 1.056 |
| 12 | 1.081 |
| 13 | 1.104 |
| 14 | 1.244 |
| 15 | 1.091 |
| 16 | 1.027 |
| 17 | 1.031 |
| 18 | 1.030 |
| 19 | 1.063 |
| 20 | 1.056 |

Mean of $d_{max}/d_{min}$: 1.112

If particle No.6, which deviates markedly from the others, is ignored, the mean sphericity of the remaining 19 particles is 1.074.

This example illustrates that absorbent cores which are among preferred type of cores in the context of the invention, viz. cassava starch cores, are available in a highly spherical quality. Inspection of these cores by microscopy also revealed a high degree of surface smoothness.

EXAMPLE 21

Determination of Degree of Gelatinization

The degree of gelatinization was estimated by measurements of the reduction in gelatinization enthalpy by differential scanning calorimetry (DSC).

About 200 mg of (a) native cassave starch (starch grains) and (b) powdered (crushed) starch cores, respectively, were weighed into respective DSC pans together with deionized water to give a 25% w/w (dry substance) slurry. The samples were sealed and heated at 1° C./min from 45° C. to 95° C. Air served as reference. Measurements were made using a differential scanning calorimeter from Hart Scientific.

The degree of gelatinization was calculated according to A. Xu and P. A. Seib [*Cereal Chem.* 70(4) (1993) pp. 463–70] as:

$H_{core}/\Delta H_{native\ starch}$, where $\Delta H_{core}$ is the endothermic enthalpy change for the (powdered) cores, and $\Delta H_{native\ starch}$ is the endothermic enthalpy change for the native starch.

The table below gives results for different batches of cassava starch cores (substantially spherical cores) from various sources, together with the estimated water-absorption capacity for the various cores (estimated, e.g., as in Example 1 herein):

| Core supplier | % Gelatinization | Absorption capacity (% w/w) |
| --- | --- | --- |
| Cia. Lorenz (Brazil) | 43 | ≧33 |
| Agro Comercial (Brazil) (1) | 53 | ≧33 |
| Agro Comercial (Brazil) (2) | 42 | ≧33 |
| Sukhjit (India) | 92 | <20 |

EXAMPLE 22

Trial Production-Scale Preparation of Savinase™/-Cassava Starch Cores 327 kg of cassava starch cores (from Cia. Lorenz, Brazil) were charged into a 1200 liter Lödige mixer equipped with 5 choppers; however, the choppers were not operated in the following:

A total of 81 kg of Savinase™ concentrate (activity 37.15 KNPU/g; dry-matter content 28.4% w/w) was sprayed onto the cores, with mixing by means of the mixing blades, at a feed rate of approximately 10 kg/min, using 2 nozzles placed in the "chimneys" in the upper part of the mixer. Mixing was continued for a further 5 minutes after stopping the spraying.

The product, which showed no sign of stickiness or tendency to agglomerate, was transferred to a drying fluid bed. After 10 minutes of drying employing air with a velocity of ca. 1.5 m/sec and an initial air inlet temperature of 60° C., the inlet air temperature was increased to 75° C. for a further 10 minutes and then to 95° C. The total drying time was 32 minutes, and the fluid bed was emptied when the bed/product temperature reached 80° C.

The dried product (raw granulate) was then sieved on a three-deck sieve, and the fraction of size ca. 300–1100 µm was coated in a 600 liter Lödige mixer as follows:

318 kg of raw granulate was introduced into the mixer. 3.8% w/w (relative to the raw granulate) of PEG 4000 was added with mixing, and the mixer was kept running for 1 minute. 12.5% w/w (relative to the raw granulate) of a powder mix consisting of 38.5% w/w of titanium dioxide and 61.5% w/w of kaolin was then added. After operating the mixer for a further 30 seconds, 0.5% w/w of PEG 4000 was added and the mixer was kept running for a further 1 minute before adding 3% w/w (relative to the raw granulate) of the above-mentioned TiO$_2$/kaolin powder mix. The mixer was then operated for a further 2 minutes.

The resulting coated product was transferred to a cooling fluid bed (air velocity ca. 1.5 m/s) with an air inlet temperature ranging from 15° C. to 20° C., and cooled therein for 31 minutes. The final product temperature was 26° C.

The cooled product was then sieved on a two-deck sieve and finally bagged. A sample of the product was examined with respect to protease (Savinase™) activity and dust level, giving the following results:

Activity: 6.56 KNPU/g
Dust (Heubach):    Total dust: 0.1 mg;    active dust: 43 μg

EXAMPLE 23

Performance of a Savinase™/Cassava Starch Granulate in Textile (Laundry) Washing In this example, the washing performance of a coated, Savinase™/cassava starch granulate of the invention (prepared and coated essentially as in Example 3 (vide supra), but containing a higher level of Savinase™), was compared with that of a standard, commercially available Savinase™ granulate (coated granulate) of a type according to U.S. Pat. No. 4,106,991 (Savinase™ 6.0T, from Novo Nordisk A/S, Denmark).

The Savinase™/cassava granulate (activity 6.81 KNPU/g) and the the Savinase™ 6.0T granulate (activity ca. 6.5 KNPU/g), respectively, were tested in conjunction with a detergent composition [Red OMO™ (compact powder) from China] for performance with respect to stain-removal from standard test swatches (EMPA117, from Center for Test Materials, Holland; white cotton/polyester stained with blood, milk and carbon black) under conditions corresponding to Japanese washing conditions (vide infra).

Red OMO™ as supplied contains enzymes, and for the purposes of the tests described herein the enzyme content was deactivated before use, as follows (amounts given are per single wash):

35 g of Red OMO™ compact powder as supplied was dissolved/-dispersed in 400 ml of deionized water with stirring at ambient temperature for 10 minutes. The solution/dispersion was then heated at 85° C. for 5 minutes in a microwave oven before use in the washing procedure.

Each swatch was attached to a black T-shirt (100% cotton) which was thus washed together with the swatch in order to examine whether any solid residue (notably cassava starch) could be detected thereon after washing. In each wash, 9 swatches/T-shirts were washed together. For control purposes, a corresponding wash was performed without any enzyme (enzyme-containing granulate) added to the washing medium.

The washing conditions are summarized below:

| | |
|---|---|
| Detergent: | Red OMO ™ (enzyme content deactivated prior to use) |
| Detergent dosage: | 1.0 g/l |
| pH: | 10.2–10.3 (not adjusted) |
| Washing time: | 12 minutes |
| Washing temperature: | 20° C. |
| Water hardness: | 6° dH Ca$^{2+}$/Mg$^{2+}$ (2:1) |
| Wash liquor volume: | 35 liters |
| Enzyme concentration in washing medium: | 10 nM |
| Washing machine: | Japanese |
| Test fabric: | EMPA117 swatches + black T-shirts (9 swatches/T-shirts per wash) |

Water of the correct hardness was prepared by adding calcium and magnesium chloride to deionized water.

The reflectance/emission, R, of the test swatches was measured at 460 nm using an Elrepho 2000 photometer (aperture 10 mm, without UV).

The results are summarized in the following table, which gives the mean of the R values for the 9 swatches/T-shirts in each wash:

| Tested granulate | Mean R value |
|---|---|
| Savinase ™/cassava starch | 60.8 |
| Savinase ™ 6.0 T | 62.0 |
| None (no enzyme) | 47.5 |

In no case was any residue visible on the black T-shirt material.

The results indicate that the washing performance of the coated Savinase™/cassava starch granulate according to the invention compares well with that of the commercial Savinase™ 6.0T granulate.

EXAMPLE 24

Crushing Strength of Cores

In this example, the resistance of various types/fractions of cassava starch cores (from Brazilian suppliers) and non-pareil cores to crushing was determined using the apparatus shown in FIG. 1 (vide infra) in the manner described earlier, above.

The crushing strengths (in g/m$^2$ given in the table below are the mean of the values for 20 particles (cores) taken at random from a batch of the core type/fraction in question. Standard deviations (SD) are also given.

| Core type (supplier) | Size range (μm) | Strength (g/mm$^2$) | SD (g/mm$^2$) |
|---|---|---|---|
| Cassava starch (Agro Comercial) | 500–600 | 1010 | 770 |
| Cassava starch (Cia. Lorenz) | 500–600 | 1495 | 619 |
| Cassava starch (Agro Comercial) | 600–710 | 1038 | 816 |
| Cassava starch (Cia. Lorenz) | 600–710 | 1662 | 754 |
| Cassava starch (Agro Comercial) | 710–850 | 1104 | 657 |
| Cassava starch (Cia. Lorenz) | 710–850 | 1600 | 565 |

| Core type (supplier) | Size range (μm) | Strength (g/mm²) | SD (g/mm²) |
|---|---|---|---|
| Non-pareil (Crompton & Knowles) | 500–600 | 93 | 88 |
| Non-pareil (NP Pharma) | 500–600 | 203 | 96 |

EXAMPLE 25

This example describes the preparation of coated, Savinase™-containing granulates (granulates according to the invention) based on potato starch cores and corn (maize) starch cores, respectively.

A: Preparation from Potato Starch Cores:

Step 1: A 15 kg portion of potato starch cores with good absorption properties (from TIPIAK, France) with a particle size range of 1.8–3.2 mm was introduced into a 50 liter Lödige mixer, where they were sprayed, with mixing at 150 rpm and without operating the chopper, with 5.0 kg of ultrafiltered Savinase™ concentrate (27.4 KNPU/g), using a two-fluid nozzle.

The product was then transferred to a Glatt WSG 5 fluid bed apparatus and dried as described previously.

Step 2: The dried granulate was coated with 4.8% w/w of PEG 4000 and 12.5% w/w of a 1:1 mixture of titanium dioxide and kaolin, as described in Example 12 (vide supra).

The active dust content (Heubach method) after coating was 35 μg.

B: Preparation from corn starch cores: A 15 kg portion of corn starch cores (from Santos, India) with a particle size range of 850–2000 μm was treated with Savinase™ concentrate, and subsequently dried, as described above in step 1 for potato starch cores.

EXAMPLE 26

This example describes the preparation of coated phytase/cassava starch granulates.

Granulate 1.

Step 1: A 3.5 kg portion of cassava starch cores (from Agro Comercial, Brazil; fraction of predominant size range 300–1000 μm) was introduced into a 20 liter Lödige mixer. The cores were sprayed, with mixing at the highest mixing speed of the apparatus, with a phytase solution prepared by dilution of a phytase concentrate (from Novo Nordisk A/S) to a concentration of 10700 FYT/g. The chopper was not operated.

Step 2: The product from step 1 was transferred to a fluid bed and dried at 60° C.

Step 3: The dried, raw granulate was coated in a Lödige mixer at ca. 80° C. with melted hydrogenated palm oil and Talc 5/0 M-10; the coating was applied in alternating layers as follows (weight percentages relative to raw granulate):

1) 5% w/w of hydrogenated palm oil;
2) 12.5% w/w of talc;
3) 1.0% w/w of hydrogenated palm oil;
4) 5.0% w/w of talc;
5) 2.0% w/w of hydrogenated palm oil;
6) 5.0% w/w of talc.

Granulate 2.

Steps 1–3: As for granulate 1, above, except that the sprayed phytase solution employed in step 1 contained 65 g of dissolved Neosorb™ 70/70.

Granulate 3.

Steps 1–3: As for granulate 1, above, except that the sprayed phytase solution employed in step 1 contained 17.5 g of dissolved polyvinylpyrrolidone (PVP K30).

Granulate 4.

Steps 1 and 2: As for granulate 2.

Step 3: Omitted

Granulate 4 thus corresponds to granulate 2, but lacks a coating.

EXAMPLE 27

In this example the retention of phytase activity of coated phytase/cassava starch granulates prepared as in Example 26 was examined and compared with that for a commercially available phytase-containing granulate (coated granulate; Phytase Novo CT, obtained from Novo Nordisk A/S, Denmark).

Granulates 1–4 as prepared in Example 26, and a Phytase Novo CT granulate were compared in a so-called pelleting test, according to a standard procedure, at Bioteknologisk Institut, Kolding, Denmark. In this test, the respective granulates are mixed with a commercial piglet feed composition, and the mixture is formulated into pellets under conditions of heat and high humidity. At 95° C., the measured retention of phytase activity deriving from the three coated, cassava-based granulates (granulates 1–3) was very similar (79–84% retention of activity), whilst the retention of activity deriving from the commercial (coated) granulate was 61%. The retention of activity deriving from the uncoated cassava-based granulate under the same conditions was approx. 52%.

This example thus demonstrates that the formulation of enzymes as granules based on starch-based cores can result in very substantial protection of the enzyme content thereof against deactivation under harsh conditions, and that granules of the type in question are very well suited to the manufacture of feed compositions which require a heat treatment (e.g to ensure removal of pathogenic organisms).

EXAMPLE 28

The granulates (four cassava-based granulates and the Phytase Novo CT granulate) employed in Example 27 were also tested with respect to ease of "dissolution" (with attendant release of phytase activity) with stirring in an acetate buffer at 37.5° C., starting with phytase activities (as granulate) of 50 FYT/ml of buffer. After 60 minutes, all four cassava-based granulates exhibited more than 90% release of phytase activity, whilst the commercial granulate exhibited slightly more than 60% release of phytase activity.

This example thus demonstrates, e.g., that starch-based granules of the type in question possess very advantageous properties with respect to the availability of the enzyme content thereof under conditions similar to those obtaining in the digestive system of an animal.

What is claimed is:

1. A process for producing an enzyme-containing granule, comprising:
   (a) contacting a starch or modified starch core with an aqueous enzyme solution or dispersion for sufficient time to result in absorption of the enzyme solution or dispersion into the starch core without agglomeration or disintegration of the starch core; followed by:
   (b) drying the enzyme-containing starch granule.

2. The process of claim 1, wherein the starch core is intrinsically capable of absorbing at least 5% of w/w of water.

3. The process of claim 1, wherein the starch core is intrinsically capable of absorbing at least 20% w/w of water.

4. The process of claims 1, wherein the starch core is intrinsically capable of absorbing at least 30% w/w of water.

5. The process of claim 1, wherein the granule has a ratio between the largest and smallest diameter of less than 3.

6. The process of claim 1, wherein the ratio between the largest and the smallest diameter of the granule is less than 1.5.

7. The process of claim 1, wherein the ratio between the largest and the smallest diameter of the granule is equal to or less than 1.2.

8. The process of claim 1, wherein the starch is gelatinized in a degree range of 2–95%.

9. The process of claim 1, wherein the degree of starch gelatinized is at least 2%.

10. The process of claim 8, wherein the degree of starch gelatinization is in the range of 10–60%.

11. The process of claim 8, wherein the degree of starch gelatinization is in the range of 30–60%.

12. The process of claim 1, wherein the degree of starch gelatinization is up to 95%.

13. The process of claim 1, further comprising adding one or more coating layers to the dried enzyme-containing starch granule.

14. The process of claim 13, comprising adding two or more coating layers to the dried enzyme-containing starch granule.

15. The process of claim 1, wherein the enzyme-containing starch granule has a size in the range of about 50–4000 micrometers.

16. The process of claim 1, wherein the size is in the range of 300–2000 micrometers.

17. The process of claim 1, wherein the starch core further comprises one or more materials selected from the group consisting of binders, fillers, plasticizers, fibrous materials and superabsorbents.

18. The process of claim 1, wherein the aqueous enzyme solution or dispersion comprises one or more enzyme selected from the group consisting of peptidases, amylases, lipases, cellulases, oxidoreductases, phytases, and xylanases.

19. An enzyme-containing starch granule produced by the process of claim 1.

20. An animal feed composition comprising the enzyme-containing granule of claim 19.

* * * * *